United States Patent
Santoianni et al.

(10) Patent No.: US 6,270,476 B1
(45) Date of Patent: Aug. 7, 2001

(54) CATHETER

(75) Inventors: Domenic Santoianni, St. Leonard; Daniel Nahon, Ottawa; Dan Wittenberger, Pierre-fonds; Jean-Pierre Lalonde, Verdun; Cristian Petre, Laval, all of (CA)

(73) Assignee: CryoCath Technologies, Inc., Kirkland (CA)

( * ) Notice: Subject to any disclaimer, the term of this patent is extended or adjusted under 35 U.S.C. 154(b) by 0 days.

(21) Appl. No.: 09/298,234

(22) Filed: Apr. 23, 1999

(51) Int. Cl.[7] .................................................. A61M 37/00
(52) U.S. Cl. .......................... 604/95.04; 606/23; 600/585
(58) Field of Search .................................. 606/20–26, 41; 600/585; 604/95.01, 95.04, 95.05; 607/122

(56) References Cited

U.S. PATENT DOCUMENTS

| | | | |
|---|---|---|---|
| 4,834,709 | * | 5/1989 | Banning et al. ...................... 604/170 |
| 5,109,830 | * | 5/1992 | Cho .......................................... 606/7 |
| 5,281,213 | | 1/1994 | Milder et al. . |
| 5,281,215 | | 1/1994 | Milder . |
| 5,322,064 | * | 6/1994 | Lundquist ............................ 600/374 |
| 5,368,049 | * | 11/1994 | Raman et al. ....................... 600/585 |
| 5,397,304 | * | 3/1995 | Truckai .................................. 604/95 |
| 5,423,807 | * | 6/1995 | Milder .................................... 606/20 |
| 5,642,736 | | 7/1997 | Avitall . |
| 5,687,723 | | 11/1997 | Avitall . |
| 5,702,438 | | 12/1997 | Avitall . |
| 5,716,353 | | 2/1998 | Matsuura et al. . |
| 5,720,719 | * | 2/1998 | Edwards et al. ....................... 604/22 |
| 5,730,127 | | 3/1998 | Avitall . |
| 5,730,704 | | 3/1998 | Avitall . |
| 5,730,719 | * | 3/1998 | Edwards ................................. 604/22 |
| 5,733,280 | * | 3/1998 | Avitall .................................... 606/23 |
| 5,738,683 | | 4/1998 | Osypka . |

* cited by examiner

*Primary Examiner*—Michael Peffley
(74) *Attorney, Agent, or Firm*—Gunster, Yoakley & Stewart, P.A.

(57) ABSTRACT

A catheter for ablating tissue, for example to treat a cardiac arrhythmia, includes a handle, a shapeable shaft and a distal ablation segment. The shaft retains a first position until manipulated to a further position with the application of moderate manual pressure. The shaft incorporates plastically deformable elements and is shapeable to conform to an insertion path or the particular anatomy of a patient for accessing a site to be ablated. Once shaped, the shaft retains its shape as the catheter is inserted or manipulated to the predetermined tissue treatment location and the distal segment is urged into contact with the tissue site. A deflection mechanism may be provided to facilitate navigation to, or to deflect the ablation segment into conformal contact with, the tissue target. In a further or alternative embodiment, a second or auxiliary shaft member extends distally from the ablation segment, allowing the segment to be threaded by or pulled past occluding tissue to a remote target tissue site. By gripping the end of the second shaft, the flexible ablation segment may be either tensioned or pulled inward against, or flexed and pushed outward against a treatment site, such as a region of the posterior epicardial wall, thus providing more effective contact for a broad range of dispositions and tissue orientations. In another embodiment, a thermal shield extends over a portion of the ablation segment, shielding adjacent tissue from damage while still effectively exposing the target tissue to ablation energy. The shield may be rotated or moved axially to delimit an area of cryogenic contact and achieve better protection of surrounding tissue structures in occluded or remote treatment target regions.

22 Claims, 3 Drawing Sheets

CATHETER

CROSS-REFERENCE TO RELATED APPLICATIONS

Not applicable.

STATEMENTS REGARDING FEDERALLY SPONSORED RESEARCH

Not applicable.

FIELD OF THE INVENTION

The present invention relates to medical devices and more particularly to devices for minimally invasive surgery. It particularly relates to catheters and catheter-like devices for contacting tissue at a distal region from an entry incision.

BACKGROUND OF THE INVENTION

Many different types of catheters are used for various diagnostic and therapeutic procedures. One type of catheter has an elongated flexible shaft with a steerable distal end for negotiating a path through the vascular network or other passageway in the body of a patient. These long and flexible catheters are well-suited for non-invasive procedures. Another type of catheter has a rigid shaft and is useful for invasive procedures where a more local opening or direct access to a treatment site is available.

While rigid catheters may be useful in some applications, they have certain limitations as well. For example, without a shape especially adapted for reaching a particular location in the body of a patient, the rigid nature of the catheter limits the area of tissue that can be reached and treated by the catheter. Even where a relatively large incision is provided, tissue areas that are not at least somewhat directly accessible cannot be reached. Although rigid catheters can include a curvable distal tip to facilitate their placement or their movement past obstructions, such a tip is relatively small and is not generally effective to compensate for the limited range of motion due to the shape of the catheter.

In one particular application, rigid catheters are used in the treatment of cardiac arrhythmias. Some invasive procedures for treating cardiac arrhythmias include positioning a rigid catheter with a deflectable distal tip through a local surgical opening against, or into, a chamber of the heart. Since the rigid catheter has a predetermined shape, one must select a catheter that has the most appropriate shape for positioning the distal tip of the catheter in contact with the treatment site in view given the particular anatomical pathway to be followed in the patient. It will be appreciated that a large inventory of rigid catheters may be required to accommodate the various treatment sites and patient anatomies. Further, for a patient having a relatively uncommon anatomic configuration and/or a difficult to reach treatment site, all rigid catheters of an existing set may well have less than optimal shapes for positioning the somewhat flexible treatment tip in suitable contact with their targeted site. This may impair the prospects of successfully carrying out the treatment procedure, especially when the treatment is one such as an ablation treatment that relies on good tissue contact and operates locally upon the contacted tissue. While a catheter having a customized shape might in theory be assembled or fabricated, in practice this would not be feasible during the procedure. Furthermore, for an ablation catheter which must bear against tissue at the remote region to ablate a lesion, the contour followed by the catheter in reaching the target site will in general further restrict the direction and magnitude of the movement and forces which may be applied or exerted on the tip itself to effect tissue contact and treatment.

It would, therefore, be desirable to provide a catheter which, while having sufficient rigidity to facilitate positioning of the catheter to a selected location within the body of a patient, is also better adapted to reach or treat the particular targeted anatomy of the patient.

BRIEF SUMMARY OF THE INVENTION

The present invention in one aspect provides an instrument having a semi-rigid, shapeable shaft that is deformable to a desired contour and yet retains its shape for positioning and operating a distal treatment segment. Although primarily shown and described as a cardiac ablation catheter, it is understood that the device has other applications as well.

In one embodiment, a catheter includes a handle having a proximal portion facilitating handling of the catheter and a distal portion coupled to a semi-rigid shapeable shaft. The shaft has a rigidity such that the shaft retains one shape until being influenced to a further shape by the application of moderate pressure on the shaft. A selectively deformable distal segment configured for ablating target tissue extends from the shaft. In an exemplary embodiment, the distal segment is deflectable by control through the shaft to deflect by an angle of more than 360 degrees, e.g., to form a loop.

In another embodiment, the distal ablation segment is adapted to removably receive a second shaft, called a shaft extension herein, which extends from its distal end. Preferably, the extension is one of a set of extensions having distinct lengths, shapes or gripping features, and which are removably attachable either before deployment of the catheter, or following deployment of the distal portion toward the target tissue region. The shaft extensions may attach by a snap plug, by a threaded junction or otherwise, to form a catheter having an active treatment segment located intermediately along the shaft. The extension fixes the distal end of the active segment, to provide a second shaft or handle so that by exerting physical force on both ends of the distal segment, the ablation segment is formed to a desired curvature, or forced into contact pressure against the target tissue which is to be treated. In a representative embodiment, the shaft extensions are provided in a range of lengths from under one inch long to several or more inches long. The shorter ones may be adapted to butt against or suture to tissue and provide a fixed point against which force is exerted for controlling the distal aspect of the ablation segment. The longer ones may be adapted for manual gripping and in this case are used to manipulate or pull the assembly around or through occluded regions of tissue, and to flex, tension or otherwise urge the distal segment into effective ablation contact against tissue to be treated.

In accordance yet another feature of the invention, a thermally insulating body is deployed over a partial circumferential aspect of the treatment segment to shield adjacent or occluding tissue. Cryogenic energy is thereby effectively applied selectively to the targeted tissue. In different embodiments, the insulating body may be a pad extending over the inner (or the outer) surface, as viewed in the sense of curvature of the distal segment, or the insulation may be a cylindrical sheath cut away on one side. Preferably the insulating body is deployable, by an axial or rotational movement along the shaft over the distal segment, to selectively insulate and prevent unwanted ablation effects at one side thereof. The invention also contemplates a thermally insulating member forming a retractable cylindrical sheath entirely surrounding the ablation segment, and effective to protect tissue as the catheter is inserted into a cardiac chamber. Thereafter the sheath is retracted to expose the tip, or to expose the entire segment, once it has been placed at the treatment site.

The catheter is well suited for surgical procedures such as forming linear ablation lesions of a surgically accessed site, especially a remote or occluded site such as the posterior cardiac wall. After examination of the patient, the catheter shaft is shaped to achieve a predetermined configuration based on the particular anatomy of the patient and the location of tissue to be ablated. The shaped catheter is inserted into the patient's body and moved to position the distal segment in contact with the intended tissue ablation site. The catheter is then actuated to treat tissue in contact with the distal segment.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
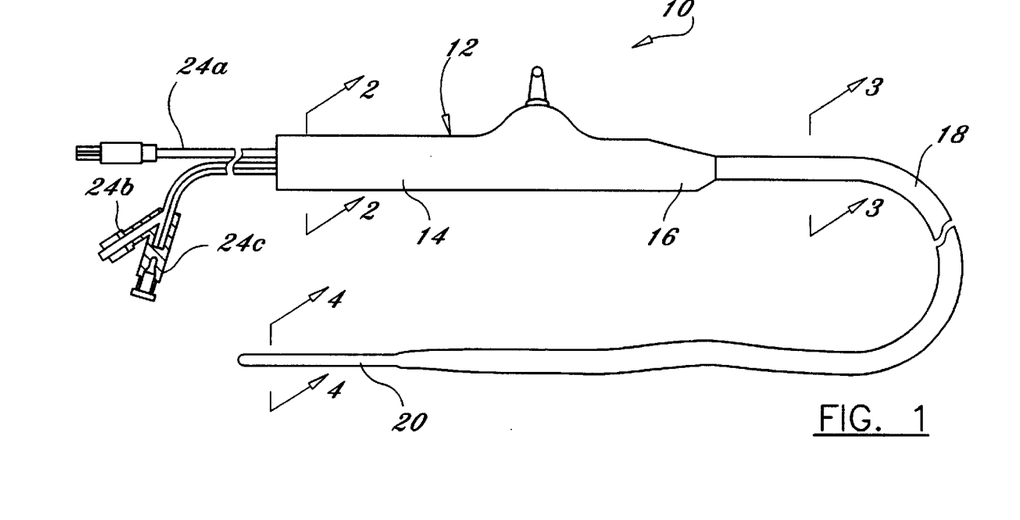
FIG. 1 is a perspective view of a first medical device in accordance with the present invention, embodied as a catheter with treatment tip.

FIG. 1 shows a first embodiment of a medical device 10 in accordance with the present invention, illustratively a catheter. The catheter includes a handle 12 having a proximal portion 14 and a distal portion 16, and in this embodiment includes a shapeable shaft 18 extending from the distal portion 16 of the handle for positioning a distal segment 20 of the catheter within the body of a patient. As described below, the shapeable shaft 18 in use is bent by a surgeon or other medical personnel into a conformation, particular for the anatomy of a patient, to access the location of the tissue to be treated and position the tip or active region of the catheter, discussed more fully below, in an orientation to treat the tissue.

Figure 2:
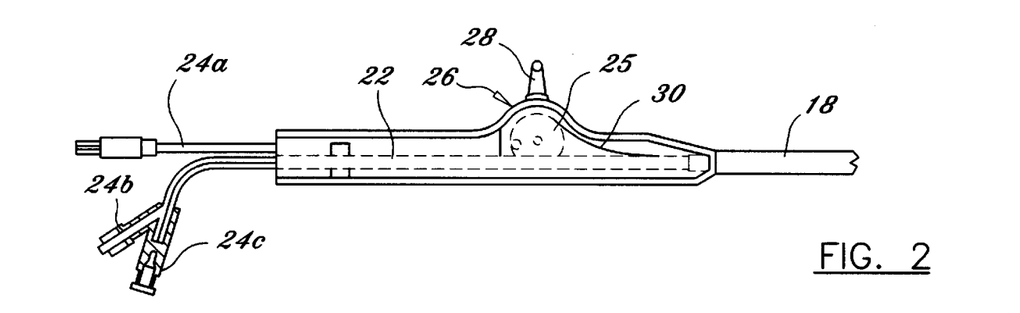
FIG. 2 is a lengthwise cross-sectional view of a handle forming a part of the catheter of FIG. 1 along line 2.

As shown in FIG. 2, the handle 12 has a central lumen 22 formed therein to accommodate a plurality of conduits, wires and/or tubes 24 that ultimately extend to the distal segment 20 of the catheter. Generally, the conduits and/or wires 24 extend proximally from the handle 12 for connection to a remote device or supply. In one embodiment, an electrical conduit 24a, a vacuum conduit 24b and a refrigerant conduit 24c extend within the lumen 22. The electrical conduit 24a provides a passageway for electrical leads to one or more devices, such as at least one thermocouple disposed within the distal segment 20 for providing temperature information. The refrigerant conduit 24c provides a passageway for a refrigerant to flow to the distal segment 20 as described below. The vacuum conduit 24b provides a return or exhaust path for the refrigerant. In addition these elements, it is to be understood that one or more further or different conduits may also be provided for additional connections to the distal segment 20.

Secured to the handle 12 of this embodiment is a steering mechanism 26 for deflecting the distal segment 20. The illustrated steering mechanism 26 includes a rotatable member 25 coupled to at least one pull wire 30 extending through the shaft 18 to the distal segment 20. This operates, as discussed further below, so that by moving the thumb lever 28 and thereby applying tension to the pull wire 30, the disposition and deflection (see FIG. 5) of the distal segment 20 are varied.

Again referring to FIG. 1, the shaft 18 of the catheter of this embodiment has a shape-holding deformability; that is, it has a rigidity such that the shaft retains a first shape until manipulated to a further shape with the application of moderate pressure, and until reshaped, it retains its shape with sufficient rigidity to manipulate the distal segment 20, urge it against tissue, and push it past intervening tissue to a desired position. It is understood that shape, as used herein, is to be construed broadly to include any contour which is needed to configure the device for reaching an obscure or distal location in the body for positioning the active or distal portion of the catheter, and may include successive bends or segments having more than one curve, angle, deformation or other non-linear configuration. The shape-retaining feature of the shaft 18 allows an operator to bend the shaft to a shape or contour, for example to reach around an organ, bone or tissue structure, and have an optimal configuration for positioning and or orienting the active or distal region of the catheter based upon the particular anatomy of a patient and the location of the treatment site. Further, the stiffness of the shaft 18 is such that the surgeon can form the shaft by hand to a desired shape without undue effort, and yet the shaft retains the set shape as the catheter is maneuvered to and held in position at the treatment site. The shaft 18 should also be sufficiently rigid such that the surgeon can place the distal segment 20 of the catheter in mild pressured contact with the tissue treatment site. That is, the shaft is sufficiently stiff to enable the surgeon to press the distal segment 20 against the tissue to be treated without inducing a further deformation in the shape of the shaft 18. The shaft may in some embodiments deflect slightly, and yet has sufficient stiffness to transfer an effective level of lateral force at its distal end.

The malleability stiffness of the shaft can vary depending upon the desired application. The plastic deformation stiffness of the shaft is generally such that a surgeon can bend the shaft by hand to a desired contour with the application of moderate pressure. However, it is understood that its stiffness may, as a whole or in particular regions, may be such that additional tools, e.g., pliers, are required or desirable for exerting enough force to change the shape of the shaft. For example, the proximal end of the shaft may be more rigid to allow it to be more forcefully navigated or positioned, and allow it to transmit more precise manual movements to the distal end, or a relatively stiff offset jag, corner or curve portion may be provided to suit the transmission of force along a preset contour of an otherwise-shapeable length of the shaft, for example to manipulate the distal shaft through a fixed and more rigid intermediate portion lying along the lateral cardiac region. The invention also contemplates that other tools, such as templates, may be used to verify that the desired shape for the shapeable portion of the catheter has been achieved. In an exemplary embodiment, the bending stiffness of the shaft 18 (characterized by the product of the modulus of elasticity and the moment of inertia) ranges from about five lb·in$^2$ to about one hundred lb·in$^2$. For example a 14 gauge copper wire can be used, or any wire with a ductility range of about 20% elongation in two inches to about 40% elongation in two inches. Suitable bending or deformation stiffnesses may, for example, be achieved by enclosing one or more bendable wires or rods, such as eight to twelve gauge soft iron or copper strands or strips within the shaft 18. Preferably, this is done by tightly enclosing the bendable members within one or more lumens extending along the tubular polymer catheter body, so that shear forces between the body and rods provides bending and holding resistance. Alternatively, a helical coil may be wrapped, for example as a flat-wound overlapping cylinder, or as a set of spaced windings embedded in an inelastic spacer polymer or plastic material. In the latter case, the friction of overlapping windings, or the deformation of the putty-like spacer material provides a bendable but shape-holding property to the shaft. The shaft may also contain a tapered shape-imparting wire or rod; in this case, the rod or rods are preferably thickest near the proximal (handle) end.

Figure 3:
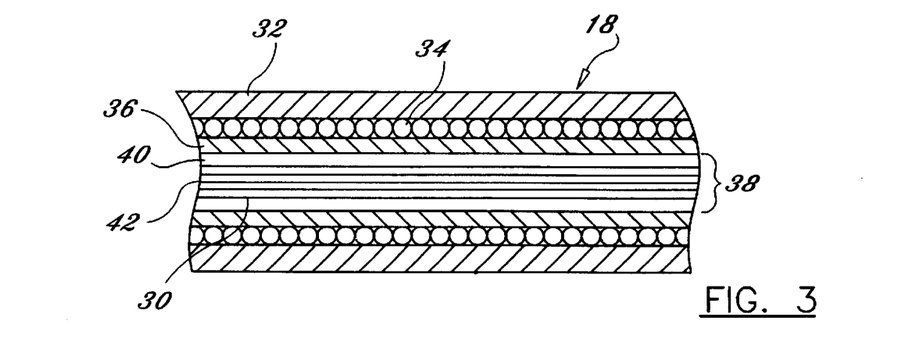
FIG. 3 is a lengthwise cross-sectional view of a portion of a shaft forming a part of the catheter of FIG. 1 along line 3.

In the embodiment of FIG. 3, the catheter is a cryoablation catheter, and the shaft 18 includes various layers and components adapted to provide the shapeable nature of the catheter, create a circulation of refrigerant through the distal segment 20 and to effect deflection of the distal segment. In an exemplary embodiment, the shaft 18 includes a biocompatible, leakproof outer jacket 32, a semi-rigid shape-retaining layer 34 which may be tubular as shown or may achieve shapeability by discrete rod or strip-like inclusions or appendages, and a braided inner layer 36 with an interior cavity or lumen 38 formed in a central portion of the shaft 18.

The outer layer 32 seals the shaft to prevent the exchange or leakage of fluids between the catheter and the patient. This outer layer 32 can be formed from a variety of biocompatible materials such as nylon, Pebax, Teflon, Pelethane, or other suitable plastic or polyer material, as would be understood by one of ordinary skill in the art.

The braided inner layer 36 provides a generally flexible, yet strong shell that prevents kinking of the catheter. Exemplary materials for the inner layer include braidable steel and other suitably flexible materials.

The shape-retaining layer 34 provides the shapeable feature of the catheter, and in helically-wound embodiments, the winding provides crush resistance, and, in some embodiments, may implemented to provide a shape-holding "goose-neck" deformability. The shape-retaining layer 34 can be a round or flat wire spring. One example of a suitable construction is to use a wire of T304 stainless steel eight thousandths of an inch in diameter, wound with a 0.101" OD and 0.027" pitch, with three dead coils at each end and a full length of 2.75". Another suitable construction may be implemented with a flat wire of T304 stainless steel having a four thousandths by fifteen thousandths rectangular cross-section and wound on a 0.101" OD with a pitch of 0.026 and a full length of 2.75". The shape-retaining layer may also be made with a machined (e.g., laser- or chemically-etched) tube in which the machine pattern imparts the desired degree of bending or torquing stiffness. For example a pattern may be cut in the tube so that it will bend in a specific plane when subject to compressive force; such force may then be conveniently applied by a sliding sheath or a pull wire construction. Materials such as stainless steel, or nickel titanium alloy are suitable. Another characteristic useful for determining suitable spring elements is the spring's stability. The stability of the spring is the maximum load which may be applied externally before the spring buckles. A spring with stability range of 0.04 lbs to about 0.1 lbs can advantageously be used for the shape-retaining layer.

In an exemplary embodiment, the shape-retaining layer 34 is formed from a helical coil and either is made with overlapping windings of flat tape that allow the coils to fit with sufficient friction so that it holds its shape when bent, or else is otherwise formed, e.g. with malleable material or putty-like filler, so the helical coil 34 holds its shape when bent.

The lumen 38 of the shaft 18 provides a passageway between the handle 12 and the distal segment 20. In one embodiment, one or more electrical leads 40 extending from a thermocouple located in the distal segment 20 are disposed in the lumen 38 to provide temperature information. A refrigerant tube 42 is in fluid communication with a source of pressurized refrigerant to provide coolant to the distal active region for effecting cryogenic tissue ablation. Also extending along the length of the shaft in this embodiment is a pull wire 30, which operates in conjunction with the tip structure described further below to deflect the distal segment 20.

Figure 4:
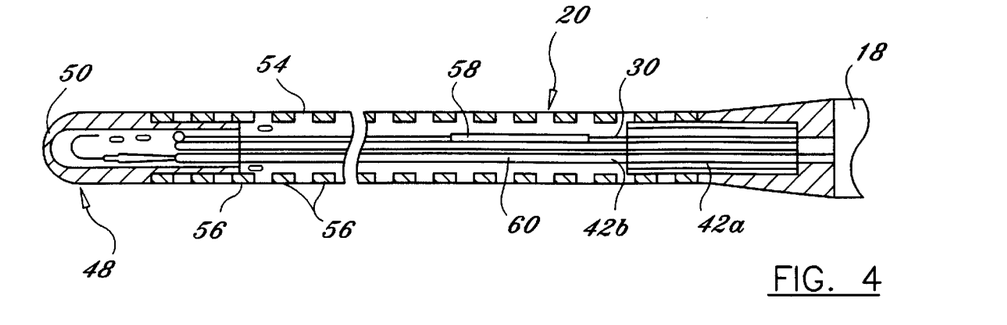
FIG. 4 is a lengthwise cross-sectional view of a distal segment forming a part of the catheter of FIG. 1 along line 4.

FIG. 4 shows further details of the distal segment 20 of this embodiment.

It is understood that for tissue ablation, the distal segment 20 can be provided in a variety of configurations to achieve a desired geometry for administering a lesion, such as an elongated lesion. Exemplary configurations for a distal segment are disclosed in co-pending and commonly assigned U.S. patent application Ser. No. 08/893,825, filed on Jul. 11, 1997, entitled CRYOSURGICAL LINEAR ABLATION STRUCTURE, which application is hereby incorporated herein by reference. However, more generally the shape of this portion may include any of the known strip, coil or basket geometries of the ablation catheter art.

Although generally shown as a cryosurgical ablation catheter, it is understood that in other embodiments the distal segment of the catheter applies other types of energy to tissue, such as RF energy, microwave energy, laser energy, and contact heating energy. It is further understood that other devices can be coupled to the distal end of the shaft other than a distal segment for ablating tissue. For example, cameras, video devices, probes and other components can be affixed to the shaft for various applications.

The deflectable distal segment 20 extends from the shaft 18 and is adapted for being positioned within the body of a patient in intimate contact along a tissue treatment site. A tip portion 48 of the distal segment is located at the distal-most part of the distal segment. The tip portion 48 has a rounded outer end 50 to ease maneuvering of the distal segment 20 within the body. The remaining outer surface of the distal segment 20 is provided by a thermally transmissive outer layer 54 formed from a flexible biocompatible material. Exemplary materials include plastics and polymers well known to one of ordinary skill in the art, such as NYLONs, silicone formulations and various forms of polytetrafluoroethylene. The outer layer 54 may advantageously be relatively thin, e.g., from about 0.0001 to about 0.001 inches in thickness. In an illustrative embodiment, the outer layer 54 may be a polytetrafluoroethylene film about one thousandth of an inch thick.

The distal segment 20 of this embodiment is structured to allow a surgeon to mechanically impart a curvature to the distal segment 20 to enhance tissue contact along its full length when creating an elongated lesion. The deflection may also be used, similarly to the "wiggler" of an endovascular catheter, for facilitating manipulation of the tip past obstructing tissue. To deflect the entirety of the distal segment, the pull wire 30 extends to a point generally proximate the tip portion 50. The pull wire 30 extends with or through a flat guide portion 58 that serves to limit the deflection of the distal segment 20 to a short length distal to the guide 58; moreover the illustrated configuration operates to deflect in a single sense or direction as the wire 30 is pulled. That is, the distal segment 20 is only deflectable in a plane generally perpendicular to a plane formed by the flat shim 60 which is positioned along the mid-plane, and deflects to the side that the pull wire is on. Thus, the shim places the distal segment normally in a flat or neutral orientation, and the pull wire acts against the inextensible /incompressible shim to curl the distal segment. The construction may be modified so that the wire both pulls and pushes, in which case the tip may be operated to curl either inwardly or outwardly, in that plane. Tension is applied to the pull wire 30 via the lever member 28 of the handle assembly (FIG. 2), to change curvature of the distal segment 20, as desired, forming a smooth curve which contacts a linear arc along the tissue to be treated. Further, the pull wire may form a completely encircling loop, enabling the distal segment to wrap around tissue or cinch a vessel.

To achieve cryogenic tissue ablation, refrigerant flows into the distal segment 20 via refrigerant tube 42. In an exemplary embodiment, the refrigerant tube 42 includes an outlet tube 42a concentric with an inlet tube 42b. The outlet or supply tube 42a connects to a source of pressurized coolant at the handle, and terminates near a proximal end of the distal segment 20, whereas the inlet or return tube 42b extends to a location proximate the tip portion 50. The coolant leaving the supply tube undergoes a phase change, and generally fills and effectively cools the distal segment 20 as it circulates via the refrigerant tube end outlet 42a, through the length of distal segment 20, to the inlet 42b, whence it returns through the shaft. A thermally transmissive helically coiled member 56 such as a flat wound metal tape provides circumferential strength and supports the outer layer 54 while simultaneously enhancing the rate of transfer of heat energy between surrounding tissue and the coolant circulating through the interior of the segment 20, for more effectively chilling and ablating tissue.

Figure 5:
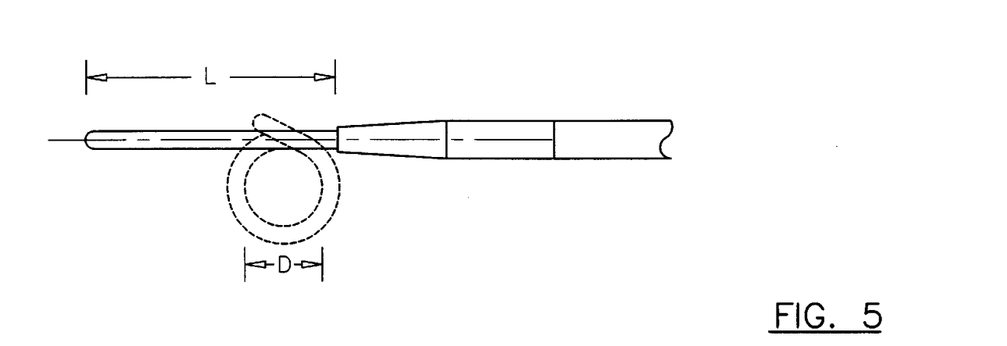
FIG. 5 is a perspective view of a portion of the catheter of FIG. 1 showing the distal segment in a deflected position.

As shown in FIG. 5, the distal segment 20 is deflectable from a linear shape to a loop shape (shown in phantom) with an angle of deflection being less than 450 degrees. To achieve full deflection of the distal segment 20, a relatively long pull, or high amount of tension is applied to the pull wire 30. At maximum deflection, a distal segment 20 having an exemplary length L of about four or five centimeters, forms a loop with a diameter D of under two centimeters.

The overall dimensions for the catheter 10 can vary. Exemplary dimensions for the shaft 18 include a length between about four inches and about twenty-five inches. The shapeable portion of the shaft can comprise all, or substantially all, of the shaft or only a small portion. The outer diameter of the shaft can range from about one eighth to about three quarters of an inch.

The length of the distal segment 20 can range from about one half inch to about two and one-half inches. The outer diameter of the distal segment can vary from about 0.05 to about 0.20 inches, and is preferably about 0.10 inches, or a 9 French.

The shapeable catheter 10 of the present invention is well suited for treating tissue in a variety of locations in the body during invasive surgical procedures. Illustrative applications include open thoracic and peritoneal surgery as well as endoscopic procedures, e.g., treating tissue located at or near the heart, intestines, uterus, and other regions for which surgical or endoscope assisted surgical access and topical tissue treatment, or cauterization or ablation is appropriate, as well as ophthalmic surgery, stripping of varicose veins and tumor ablation and various applications preparatory to further surgical steps.

In an illustrative application, the catheter 10 is used to treat cardiac arrhythmias during an open chest surgical procedure to perform linear ablations of the epicardial wall. The patient will in general be examined, for example with known cardiac mapping, fluoroscopy and soft tissue imaging techniques, or such techniques in conjunction with a cold mapping catheter having the structure of the present invention together with mapping electrodes, so as to determine accurate anatomic heart characteristics and signal pathways, and to identify and map the location of tissue to be treated. Based on the patient's anatomy and treatment site, the catheter is shaped to achieve an optimal configuration for reaching and orienting the active segment 20 in physical contact with the target tissue for ablating a line or contour.

To access the treatment site, an opening is formed for insertion of the catheter into the patient's body. For example, to ablate a linear ablation line on the wall of the atrium, a chest opening provides access to the heart. The catheter may be inserted into the atrium via a local cut to form, for example, an elongated lesion on the atrial wall. Most preferably, however, the catheter of the present invention is used to form epicardial ablation lines, for example to reach around to the posterior outer surface of the heart and form ablation lines in an occluded region. In an illustrative treatment, the distal segment 20 brought into contact with the desired ablation site and maintained at a temperature (as measured internally of the segment) ranging from about –60 degrees Celsius to about –70 degrees Celsius, while resting in contact with the tissue site for a period of several minutes, e.g., about five minutes. The temperature as measured inside the tip may be correlated with a somewhat higher tissue interface contact temperature by empirical calibration measurements if desired in order to implement various treatment control regimens.

In accordance with another embodiment of this aspect of the invention, the shaft is rendered shapeable by the inclusion of plural malleable wires or rods set within one or more parallel lumens of the shaft 18. The wires or rods, which may be formed of polymer or of a metallic material, are preferably tightly fitted or even bonded within their respective lumens such that when the shaft is bent, the relative changes in position amongst the rods as each slides differently result in a distribution of shear or strain within the material of the shaft wall, thus potentially allowing a construction of greater intrinsic strength and smaller diameter to achieve the desired bending and shape holding characteristics for positioning the ablation segment.

Figure 6:
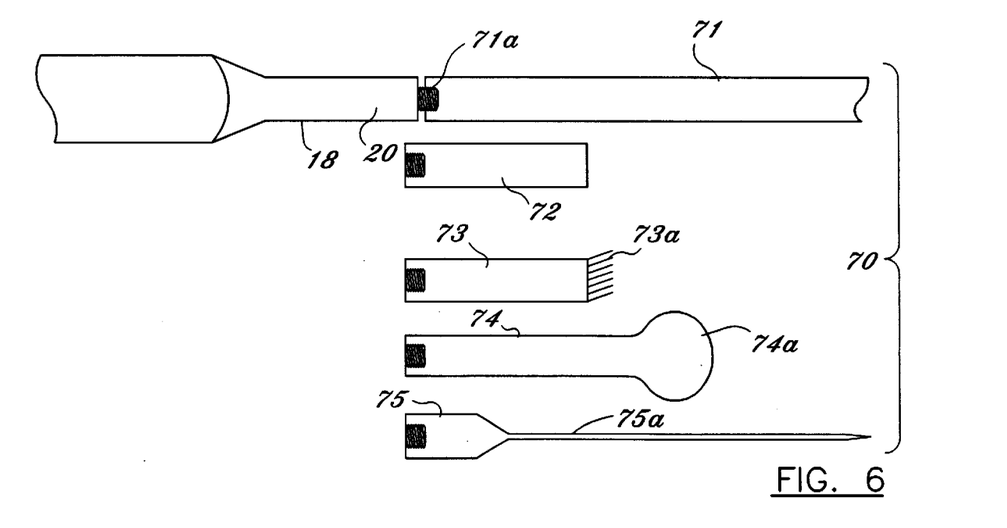
FIGS. 6 and 6A show an embodiment having a shaft extension.

In accordance with yet another aspect of the invention, the distal segment 20 is adapted to removably receive one or more auxiliary shaft segments 70 of which a representative set are shown in FIG. 6. Each auxiliary shaft segment 70 is preferably adapted to removably attach to the distal end of the distal segment 20, and in various embodiments, the auxiliary segments may have one or more of the structures indicated below.

The distal shaft segments 70, of which several are indicated among the set of segments 71, 72, 73 . . . , may include handling or positioning feature characteristics, or both.

One such embodiment 71 is simply a long cylindrical rod-like extension, which may be shapeable but somewhat rigid shaft like shaft 18, or may be simply a stiff and somewhat flexible rod. As shown, extension 71 attaches, for example, by screw threads 71a, to the distal end of the distal segment 20 and thus, mechanically speaking, pins the distal segment end so that forces on the auxiliary shaft 71 will push, pull or bend the segment. The auxiliary shaft may extend for a sufficient distance to wrap around behind the treatment site and be gripped and held by hand so that the distal segment 20 is controlled both by manipulation of the shaft 18 and of the auxiliary shaft 70. In this case, when the distal segment 20 has been brought to location at a target tissue, the auxiliary segment attached to the distal end may be pulled to urge the inner-facing surface of the distal segment against the targeted tissue. Similarly, by pushing on the auxiliary segment, one causes an outer facing side of the distal segment to rest solidly against tissue. Preferably, the auxiliary shaft segment is attached to the ablation segment prior to deployment, and may be used, like a tunneling or guide wire, to guide and navigate the catheter assembly through or around tissue—for example to weave between pulmonary veins and be pulled around behind the posterior surface of the heart. Attachment or the use of the auxiliary shaft 71 may be accomplished in several fashions. For example, according to an alternative protocol for use of the segment, the shaft 18 and distal segment 20 are advanced to the treatment site and an auxiliary opening is made if necessary, to allow the shaft 71 to be pushed and/or rotated into connection with the distal end of the segment 20. In accordance with another more typical method of use, however the auxiliary shaft is first connected, after which the active segment 20 is moved by pushing or pulling the auxiliary segment 71, and pushing on the shaft 18 to move the distal segment 20 to a desired location contacting the target tissue. Once the distal segment 20 is moved to the treatment site, it may then be further pulled to tension it against, or pushed to flex it into contact with, the target tissue.

In accordance with another embodiment of this aspect of the invention, one embodiment of an auxiliary shaft segment may be a short stub-like auxiliary shaft 72 as further shown in FIG. 6. Such an extension may, for example, have a length of one to three inches, and in use be configured to provide a foot or stable portion which bears against the surrounding tissue to fixedly hold the distal end of segment 20, so that manipulation of the handle 12 and shaft 18 causes the distal segment to assume an appropriate curvature and lie with sufficient force against the tissue being targeted. For example, when the catheter is deployed through a small surgical opening in a minimally invasive approach to form an epicardial lesion or to ablate tissue in the thoracic cavity, the auxiliary shaft segment 72 may be adapted to extend for the remaining length of the thoracic cavity, for example to bear against the spine or rib cage, and thus stabilize and fix the distal end of segment 20 so that the pressure applied from the shaft, rather than introducing an unconstrained fishing-rod or whip-like movement, bends the distal segment in a well-defined and fixed position to exert greater force along a curved pathway against the epicardial tissue which is to be ablated.

The invention also contemplates that the auxiliary shaft segments may include one or more structural features to enhance their utility in this aspect. For example, the distal tip of an auxiliary shaft segment may include a tissue fixing foot or gripping protrusion 73a as shown for shaft segment 73. This may for example, consist of a number of micro barbs or teeth which allow the tip, when pushed axially against tissue, to firmly grip the tissue and thus fix the end point position of the assembly. A blunt bulb or other such termination may alternatively be provided, which serves simply to define a non-traumatic stop member 74a for the end of the assembly 74, or a filamentous wire 75a as shown in extension 75. Other shaft extensions contemplated by applicant include extensions having suture eyelets or clips for fastening to adjacent tissue. In addition, the shaft extensions may be filled with radiographically opaque material to allow fluoroscopic or other visual determination of the site being treated. When used in any of the foregoing fashions, the auxiliary shaft segments 70 further serve to precisely control and limit the area of tissue which may be ablated by the distal segment 20, providing a safety buffer so that tissue lying distal to the target site is not inadvertently damaged by the moving catheter.

Figure 6A:
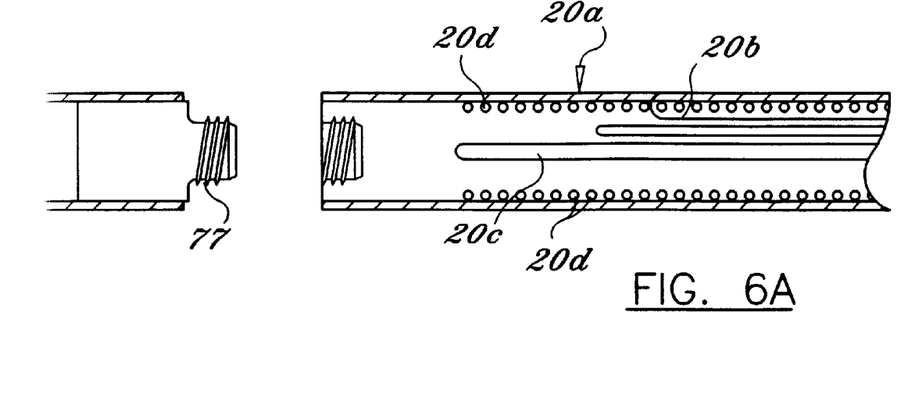

FIG. 6A illustrates a detail of one construction of a distal segment 20a and extension. As shown, the distal segment 20a of this embodiment includes a central anti-kinking stiffening shim or wire 20c but no active deflection control, a spring layer 20d, and a thermocouple temperature sensing assembly 20b in a cryogenic ablation segment. At the distal end of the segment an internal screw thread receives the mating plug 77 of the extension shaft 76, which may, for example, be a length of tubing or other extension as discussed above.

Figure 7:
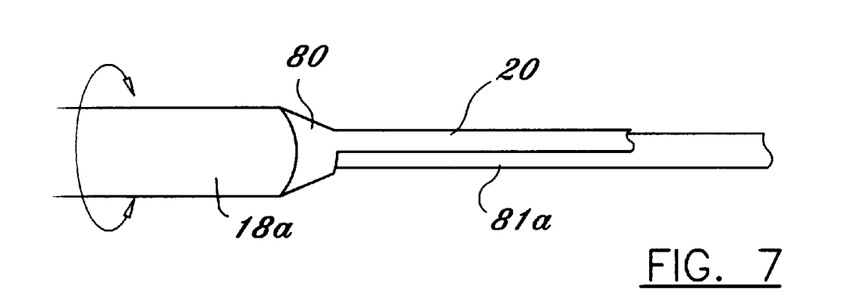
FIG. 7 and 7A show an embodiment having an insulating member.
Figure 7A:
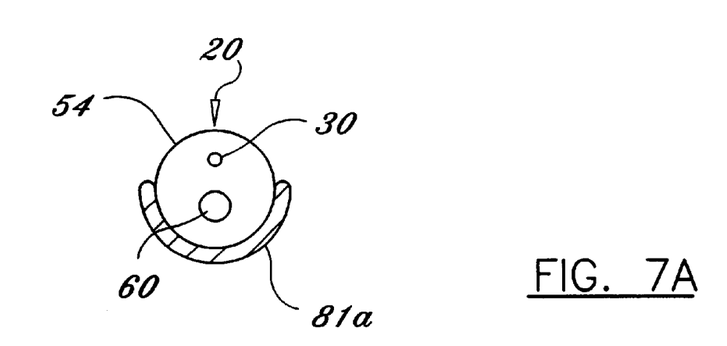

In accordance with yet another aspect of the invention, particularly directed to the cryogenic ablative properties of distal segment 20, the heat distribution during cryogenic treatment of tissue is further controlled by the deployment of a thermally insulating sheath extending over a partial circumference of the distal segment 20. FIG. 7 illustrates details of one such construction. As shown in FIG. 7, a shaft assembly 18a of a catheter assembly is shown, which may, for example, be similar to that of FIG. 1, extending to a linear cryogenic ablation or treatment segment 20, which may also be similar to that of FIG. 1. In this embodiment, an insulating sheath 80 carried by the shaft 18a extends along the length of the distal segment 20 forming a partial circumferential blanket or insulating pad 81a which prevents cryogenic action from affecting tissue on one side of the distal segment, while leaving the other side exposed for cryogenic contact with tissue. The sheath may be formed of a fibrous or insulating polymer, such as an expanded PTFE tube ten or twenty mils thick, or of an insulating material enclosed in a thin PTFE membrane. The sheath may also include a thin layer of more conductive material, such as a metal, to achieve sufficient stiffness for mechanically moving or varying the position of the shield. However, in that case the metal is insulated on at least one side to limit the rate of thermal transport there across.

While not specifically illustrated, the partial sheath so may be adapted to diverse different linear ablation segments, both internally deflectable as in FIG. 1, and to segments not having deflection mechanisms, and to segments with or without an auxiliary shaft segment 70 of the type shown in FIG. 6. As further shown in FIG. 7, the insulating partial sheath 80 is preferably deployable, for example, by rotation of a stiff outer sheath or envelope member in the shaft portion or handle, so that the insulation is rotated, as shown by arrow R, to selectively cover either the top, bottom or one side of the ablation segment 20, or is advanced or retracted along an axial direction indicated by arrow A, so as to expose the tip, or to occlude a greater or lesser length of the segment 20.

It should be noted that in the constructions described above, a principal intended use is for epicardial ablation of linear regions, wherein the ablated tissue line serves to disconnect an auxiliary pathway or other anomalous signal conduction path of the cardiac tissue, and to thereby eliminate abnormal cardiac conduction patterns such as occur, for example, in the etiology of atrial fibrillation. While the embodiment of FIG. 1 is well suited to use either epicardially or by local surgical insertion into a cardiac chamber, the auxiliary shaft segments 70 of the embodiment of FIG. 6 are well-adapted to controlling the travel and conformation of the distal segment 20 without the provision of other control mechanisms (e.g. the shim and pull wire) exerted through the handle. Thus, for example, the embodiment of FIG. 6 may be implemented with a distal segment 20 in which simply a shim or Nitinol wire is provided to assure flexibility without kinking, but without a bending or deflecting pull wire mechanism. Tissue contact and navigation of the catheter are effected solely using the shaft 18 connected to one end, and the auxiliary shaft segment 70 connected at the other end. In this manner the distal segment 20 may be, for example, inserted or interwoven between pulmuory veins to a position on the posterior cardiac surface and brought into intimate contact with the epicardial wall. In that position, the insulating sheath 80 of FIG. 7 serves as an insulating blanket to prevent excessive cooling of the lungs, spine, vasculature or other non-cardiac tissue adjacent to the treatment site behind the cooling segment 20.

Having described the preferred embodiments of the invention, it will now become apparent to one of ordinary skill in the art that other embodiments incorporating the inventive concepts may be used. The invention is not limited in spirit or scope to the disclosed embodiments but rather is to include all such variations and modifications as will naturally occur to those skilled in the art, as defined by the claims appended hereto and their equivalents in the art.

What is claimed is:

1. A catheter for tissue ablation, such catheter comprising
   a handle
   a primary shaft extending from the handle
   an ablation segment, having a proximal end and a distal end, the proximal end of the ablation segment extending from a distal end of the primary shaft and configured to receive ablation energy therethrough for ablation of tissue contacting the segment, and
   a second shaft coupled to the distal end of the ablation segment, wherein the second shaft is configured to extend from the distal end of the ablation segment such that by moving the primary shaft and the second shaft the ablation segment is spatially stabilized by the positioning of the primary shaft and the second shaft to be in contact with tissue for forming tissue ablation.

2. A catheter according to claim 1, wherein the primary shaft is formable to a shape-retaining contour for positioning the ablation segment to ablate remotely targeted tissue.

3. A catheter according to claim 2, wherein the primary shaft includes cryogenic passages for circulating a heat transfer medium through the ablation segment.

4. A catheter according to claim 3, wherein the second shaft includes means for fixing said second shaft in position against tissue.

5. A catheter according to claim 4, wherein the second shaft is elongated and flexible for enhanced movement around tissue to position the ablation segment posteriorly of an organ accessed through an anterior opening.

6. A catheter according to claim 1, wherein the second shaft is internally filled with radiographically opaque material.

7. An epicardial ablation device, comprising:
   a handle having a proximal portion and a distal portion;
   a shaft having a proximal end extending from the distal portion of the handle and a distal end, the shaft having a stiffness such that the shaft retains a first shape until manipulated to a further shape by a user manually applying pressure to the shaft, wherein the further shape is conformable to an anatomy of a patient;
   a steering mechanism; and
   a distal segment extending from the distal end of the shaft, said distal segment being coupled to the steering mechanism, and said distal segment being continuously flexibly deflectable, the deflection of said distal segment being controllable to contact tissue along an ablation line for treatment thereof.

8. A medical instrument, comprising:
   a shaft having a proximal end and a distal end, the shaft having a malleable conformations such that the shaft retains a first shape until manipulated to a second shape, and being sufficiently rigid for pushing the distal end,
   a handle coupled to the proximal end of the shaft, the handle having a steering mechanism,
   a distal segment coupled to the distal end of the shaft, the distal segment having a transitionable radius of curvature, and
   a pull wire having a proximal end and a distal end, the proximal end being coupled to the steering mechanism, and the distal end being coupled to the distal segment, the radius of curvature of the distal segment being continuously transitionable from a first position to a second position,
   the handle, shaft, pull wire and distal segment forming a catheter, and operable by shaping the shaft to position the distal segment in contact with tissue.

9. The instrument according to claim 8, wherein the shaft is manually shapeable with the application of moderate pressure.

10. The instrument according to claim 8, wherein the shaft has bending stiffness in the range from about five pound-inches$^2$ to about one hundred pound-inches$^2$.

11. The instrument according to claim 10, wherein the distal segment has an outer diameter ranging from about 0.05 to about 0.20 inches.

12. The instrument according to claim 8, wherein the distal segment is an ablation segment and the shaft is shapeable to achieve a configuration for reaching around a heart to effectively position the distal segment against the posterior epicardial wall.

13. The instrument according to claim 8, wherein the shaft has a maximum angle of curvature of about 180 degrees in a plane, and a minimum radius of curvature of about 0.25 inches.

14. The instrument according to claim 8, wherein the shaft has a length of between about four and about twenty-five inches.

15. The instrument according to claim 14, wherein the shaft has an outer diameter ranging from about one eighth inch to about three quarter inches.

16. The instrument according to claim 8, wherein the shaft comprises a shape-retaining structure including a helical coil.

17. The instrument according to claim 8, wherein the shaft comprises a shape-retaining structure including a malleable wire rod.

18. The instrument according to claim 17, wherein the malleable wire rod is tapered.

19. The instrument according to claim 8, wherein the distal segment is deflectable so as to form a loop.

20. The instrument according to claim 19, wherein the loop has a radius below about one centimeter.

21. The instrument according to claim 8, further comprising an auxiliary segment removably attached to the distal segment for positioning the distal segment in contact with tissue.

22. The instrument according to claim 8, wherein the catheter is a cryogenic ablation catheter, and the shaft includes passages for circulating a coolant through the distal segment.

* * * * *